United States Patent [19]
Heath et al.

[11] Patent Number: 5,939,062
[45] Date of Patent: *Aug. 17, 1999

[54] TRAPPING SYSTEM FOR FRUIT FLIES

[75] Inventors: Robert R. Heath; Nancy D. Epsky, both of Gainesville, Fla.

[73] Assignee: The United States of America as represented by the Secretary of Agriculture, Washington, D.C.

[*] Notice: This patent issued on a continued prosecution application filed under 37 CFR 1.53(d), and is subject to the twenty year patent term provisions of 35 U.S.C. 154(a)(2).

[21] Appl. No.: 08/440,023

[22] Filed: May 12, 1995

Related U.S. Application Data

[62] Division of application No. 08/231,213, Apr. 22, 1994, abandoned.

[51] Int. Cl.[6] .................. A01N 25/02; A01N 25/10
[52] U.S. Cl. .................. 424/84; 424/405; 424/406; 424/408; 424/410; 424/719; 424/721; 514/554; 514/663
[58] Field of Search .................. 424/410, DIG. 10, 424/408, 405, 406, 84, 719, 721; 514/554, 556, 557, 663

[56] References Cited

U.S. PATENT DOCUMENTS

| | | | |
|---|---|---|---|
| 3,989,498 | 11/1976 | Cox | 424/76.6 |
| 4,205,066 | 5/1980 | Hennart et al. | 424/84 |
| 4,950,588 | 8/1990 | Dattagupta | 435/6 |
| 5,243,781 | 9/1993 | Carter | 43/122 |
| 5,407,816 | 4/1995 | Bringi et al. | 435/123 |

OTHER PUBLICATIONS

Robacker et al J. Chem. Ecology vol. 22#3 1996 Attractiveness To Mexican Fruit Flies of Combinations of Acetic Acid with Ammonium/Amion Acid Attractants.

Mulla et al. Field Evaluation of Chemical Attractants against the fly Fannia Femoralis (Diptera: Muscipae) J. Chemical Ecology pp. 349–360 vol. 10, #2, 1984.
Quresht et al., Chemical Abstracts, vol. 88, 1977, #59400.
Winder, Chemical Abstracts, vol. 76, 1972, #149932.
Suzuki et al., Chemical Abstracts, vol. 113, 1989, #226435.
Chapman et al., Chemical Abstracts, vol. 118, 1993, #118910.
Heungens, Chemical Abstracts, vol. 122, 1994, #207683.
Kinzer et al., World Patent abstracts of U.S. pat. #4, 122, 165, 1978.
Bailey et al., Chemical Abstracts, vol. 74, 1971, #63459.
Path, World Patent abstracts of DD 203811, 1982.
Robacker et al., Chemical Abstracts, vol. 120, 1994, #156658.
Suzuki, World Patent of JP 63258642, 1988.
Anonymous, Florida Fruit Fly Detection Manual, USDA, APHIS, PPQ & FLDACS, DPI, Gainesville, FL 1989.
Baker et al., Journal of Economic Entomology 83: 2235–2245, 1990.
Bateman & Morton, Aust. J. Agric. Res. 32:883–903, 1981.
Beroza et al., J.Agric. Food Chem. 9: 361–365, 1960.
Box et al., Statistics for Experimenters: An Introduction to Design, Data Analysis, and Model Building, J. Wiley & Sons, NY, 1978.
Buttery et al., J. Agric. Food Chem. 31:689–692, 1983.
Christenson & Foote, Annual Review of Entomology 5:171–192, 1960.

(List continued on next page.)

Primary Examiner—Neil S. Levy
Attorney, Agent, or Firm—M. Howard Silverstein; John D. Fado; Gail E. Poulos

[57] ABSTRACT

A dry insect trap for capturing male and female frugivorous pest insects for detecting, monitoring, and/or controlling.

3 Claims, 11 Drawing Sheets

OTHER PUBLICATIONS

Greany et al., Entomol. Exp. Appl. 21: 63–70, 1977.
Heath et al., Journal of Chemical Ecology 17: 1925–1940.
Jones et al., Bulletin of Entomological Research 73:97–106, 1983.
Keiser et al., Journal of Economic Entomology 69: 517–520, 1976. Replaces Keiser et al., Lloydia 38: 141–152, 1976.
Kydonieus, Agis F., Controlled Release Pesticides, Scher [ed.], ACS Symposium Series 53, American Chemical Society, Washington, DC. 152–167. 1977.
Landolt et al., Environmental Entomology 21:1154–1159, 1992.
Leonhardt et al., Insect Pheromone Technology: Chemistry and Applications, ACS Symposium Series 190, American Chemical Society, Washington, DC. 159–173. 1982.
Mazomenos & Haniotakis, Journal of Chemical Ecology 11:397–405, 1985.
Mazor et al., Entomol. Exp. Appl. 43: 25–29, 1987.
McPhail, Journal of Economic Entomolgy 32: 758–761, 1939.
Morton & Bateman, Aust. J. Agric. Res. 32: 905–916, 1981.
Nakagawa et al., Journal of Economic Entomology 63: 227–229, 1970.
Nakagawa et al., Entomol. Exp. Appl. 24: 193–198, 1978.
Prokopy, Environmental Entomology 1: 720–726, 1972.
Prokopy, Canadian Entomologist 109: 593–596, 1977.
Prokopy & Boller Journal of Economic Entomology 64: 1444–1447, 1971.
Prokopy & Economopoulos, Z Ang. Entomol. 80: 434–437, 1976.
Riedl & Hislop, Environmental Entomology 14: 810–814, 1985.
Reissig et al., Environmental Entomology 11: 1294–1298, 1982.
SAS Institute, SAS/STAT Guide for Personal Computers, ver. 6 ed., SAS Institute, Cary, NC, 1985.
Steyskal, Florida Entomologist 60: 11–16, 1977.

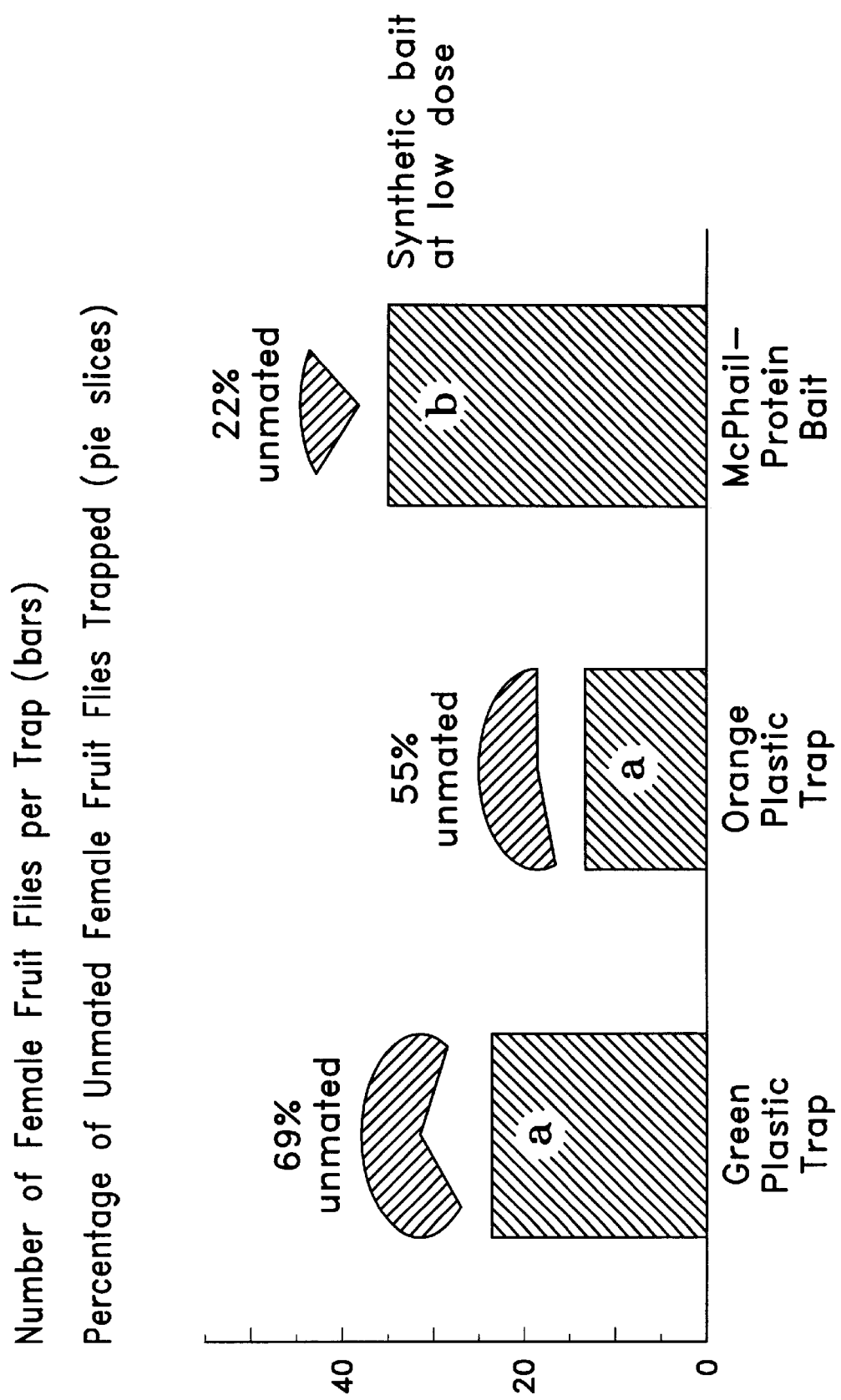

TRAPPING SYSTEM FOR FRUIT FLIES

This application is a divisional of Ser. No. 08/231,213 filed Apr. 22, 1994, now abandoned.

BACKGROUND OF THE INVENTION

1. Field of the Invention

The present invention relates to a novel method and apparatus for monitoring and/or controlling tephritid fruit flies using chemical and visual stimuli.

2. Description of the Art

Control of frugivorous pest flies is of considerable economic importance for fruit and vegetable production and export. Quarantine and regulatory agents expend substantial efforts to detect newly introduced species of economically important fruit flies. The Mediterranean fruit fly, *Ceratitis capitata* is a major frugivorous pest due to its wide distribution and large host range (Enkerlin et al., World Crop Pests, Vol. 3A; Fruit Flies, Their Biology, Natural Enemies and Control, Elsevier Science Publishers, 1989). Because of its threat and the potential for its introduction into the United States, much emphasis has been placed on detection and eradication of *C. capitata*. The development of improved lures is needed to monitor and suppress populations of this and other pest fruit flies, and to prevent establishment of populations in areas that are currently without these pests.

Methods developed for monitoring, controlling, and eradicating frugivorous fruit flies (Tephritidae) have relied extensively on the use of chemical attractants. Methyl eugenol plus dibrom; cuelure plus dibrom; ammonium salts; and a mixture of 1,7-dioxaspiro [5.5] undecane with α-pinene or n-nonanal; and spiroacetal are used as lures for species of Dacus. A composition of hexyl acetate, (E)-2-hexen-1yl acetate, butyl 2-methylbutanoate, propyl hexanoate, hexyl propanoate, butyl hexanoate, and hexyl butanoate is used as a lure for species of Rhagoletis. Trimedlure (Beroza et al., J. Agric. Food Chem. 9:361–365, 1960) is used to attract male Mediterranean fruit flies. Although trimedlure is effective in attracting male Mediterranean fruit flies, it is either only weakly active in attracting or is completely ineffective in attracting female Mediterranean fruit flies (Nakagawa et al., Journal of Economic Entomology 63: 227–229, 1970). Conventional lures currently used to survey and detect frugivorous pests are protein baits such as fermenting yeast hydrolysate (Greany et al., Ent. exp & Appl. 21:63–70, 1977) and protein hydrosylate (McPhail, J. Econ. Entomol. 32:758–761, 1939). The problem with protein lures is that they capture large numbers of nontarget insects. Furthermore, the only lures that are available for attracting both female and male fruit flies are protein baits.

Adult fruit flies require sugar to survive (Christenson & Foote, Annual Review of Entomology 5:171–192, 1960), and honeydew secreted by homopterous insects is recognized as an important food source for adult tephritids (Christenson et al., Annual Review of Entomology 5:171–192, 1960). Female fruit flies also require protein to ensure fecundity, and this protein requirement is the primary basis for traps for detection of female fruit flies. McPhail traps, bell-shaped glass traps with a water reservoir (Newell, Journal of Economic Entomology 29:116–120, 1936), baited with protein bait are currently used for monitoring fruit flies throughout fruit growing areas of the world. McPhail traps are cumbersome and use of these traps have numerous disadvantages. Servicing the trap requires that water and bait be added in a somewhat maladroit manner in which the trap is turned upside down, bait added and then the trap returned to an upright position. This process often results in bait spillage, and the spilled bait becomes a food source for flies outside the trap. Removal of insects trapped also requires considerable effort as the contents of the trap have to be filtered through a mesh screen to separate the insects from the bait solution. Protein bait solutions capture a large number of non-targeted insects and considerable time is required to sort the pest fruit flies from the non-targeted insects. The fruit flies recovered from these traps are often severely decomposed with parts missing. This increases the difficulty of differentiating marked sterile flies from unmarked fertile flies when these traps are used in conjunction with sterile insect release programs. Other factors that contribute to the difficulty in the deployment of McPhail traps include the size and weight of the trap and the fragile nature of glass.

Hundreds of compounds are known to be released from protein baits (Morton & Bateman, Aust. J. Agric. Res. 32:905–916, 1981). Examples of some volatile components of commercial hydrolyzed protein insect baits are phenylacetaldehyde, acetic acid, furfuryl alcohol, 2-acetylfuran, benzaldehyde, methanol, 2-acetylpyirole, furfural, 5-methyl-2-phenyl-2-hexenal, 5-methyl-2-[(methylthio)methyl]-2-hexenal and ammonia. Ammonia (Bateman & Morton, Aust. J. Agric. Res. 32:883–903, 1981; Mazor et al., Entomol. Exp. Appl. 43:25–29, 1987), acetic acid (Keiser et al., Lloydia 38: 141–152, 1976), and various other volatiles (Buttery et al., J. Agric. Food Chem. 31: 689–692, 1983) have been investigated as attractants for fruit flies. These reports, however, do not provide information regarding released amounts or ratios of the compounds tested or the effectiveness of these chemicals as compared to McPhail traps.

A number of tephritid fruit flies are known to be attracted to certain colors and shapes as visual mimics of foliage or fruit. It has been reported that tephritid species such as the Caribbean fruit fly, *Anastrepha suspensa* (Loew); the apple maggot fly, *Rhagoletis pomonella* (Walsh); the European cherry fruit fly, *R. cerasi* (L.); the Mediterranean fruit fly, and the olive fruit fly are attracted to yellow rectangular panels, i.e. two-dimensional visual cues mimicking foliage (Greany et al., Entomol. Exp. Appl. 21: 63–70, 1977; Prokopy, Environmental Entomology 1: 720–726, 1972; Prokopy & Boller, Journal of Economic Entomology 64: 1444–1447, 1971; Prokopy & Economopoulos, Z Ang. Entomol. 80: 434–437, 1976). Painted spheres, i.e., three-dimensional visual cues mimicking host fruit, have been reported to be attractive to the apple maggot fly (dark red spheres); the walnut husk fly, *R. completa* Cresson, (green spheres); and the Mediterranean fruit fly (black or yellow spheres) (Prokopy, Canadian Entomologist 109: 593–596, 1977; Riedl & Hislop, Environmental Entomology 14: 810–814, 1985; Nakagawa et al., Entomol. Exp. Appl. 24: 193–198, 1978). Currently all traps using visual cues either singularly or in combination with chemical attractants rely on the use of sticky materials to retain the captured insects. These materials are difficult to use and the traps need constant maintenance to remove numerous non-targeted flies captured as well as need to replenish the sticky material.

Some species of fruit flies have been trapped with a combination of visual stimuli of fruit or foliage mimics and non-pheromonal chemical lures. Reissig et al., Environmental Entomology 11:1294–1298, 1982, disclose trapping apple maggot flies using red spheres baited with synthetic apple volatiles. Riedl & Hislop, supra, reported that the addition of ammonium carbonate as a food-based stimulus enhanced the response of walnut husk flies to yellow rectangles and green spheres but there was a loss of selectivity for the walnut husk fly. Nakagawa et al., supra, reported that the addition of the chemical lure trimedlure to yellow rectangles or black spheres enhanced attraction for male Mediterranean fruit flies. Combinations of pheromone-based lures with visual mimics have been reported. Successful field testing of sex pheromone baited traps for males of the olive fruit fly, *Dacas oleae* (Gmelin) has been demonstrated using the female-produced pheromone (Jones et al., Bulletin of Entomological Research 73:97–106, 1983; Mazomenos & Haniotakis, Journal of Chemical Ecology 11:397–405, 1985). Trapping of female fruit flies based on male-produced pheromone in combination with a sphere as a visual cue has been reported for the Mediterranean fruit fly (Heath et al., Journal of Chemical Ecology 17:1925–1940) and the papaya fruit fly, *Toxotrypana curvicauda* Gerstaecker, (Landolt et al., Environmental Entomology 21:1154–1159, 1992). Attraction of female fruit flies to male pheromone occurs only when the female fly is physiologically ready to mate. Thus, female fruit flies may be attracted to male-produced sex pheromone for only brief periods of their adult life span, and none are currently in use for standard trapping procedures.

To date, there is no food-based attractant system for both male and female fruit flies that does not use either aqueous bait solution in glass traps or synthetic chemicals in traps with sticky material to capture these fruit flies. Thus more convenient methods are needed to provide a "dry" insect trap for monitoring the Mediterranean fruit fly.

SUMMARY OF THE INVENTION

It is, therefore, an object of the present invention to provide a trap for monitoring and/or controlling frugivorous pest insects using a food-based chemical stimulus.

Another object of the present invention is to provide a combination of visual and chemical stimuli that attracts frugivorous pest insects and induces them to be trapped.

A further object of the present invention is to provide a cylindrical trap for frugivorous pest insects containing a food-based chemical bait.

Still another object of the present invention is to provide a trap for frugivorous pest insects that contains a food-based chemical bait made up of ammonium acetate and 1,4 diaminobutane (putrescine).

Another object of the present invention is to provide a trap for frugivorous pest insects that includes an interior toxicant panel.

Still another object of the present invention is to provide a trap for selectively capturing sexually-immature unmated, sexually-mature unmated, or sexually-mature mated fugivorous pest insects.

A further object of the present invention is to provide a composition for attracting fugivorous pest insects that includes ammonium acetate and 1,4 diaminobutane.

Another object of the present invention is to provide a paintable aqueous composition containing a feeding stimulant, a toxicant, and a pigment for killing frugivorous pest insects.

Further objects and advantages of the invention will become apparent from the following description.

BRIEF DESCRIPTION OF THE DRAWINGS

FIG. 5a shows the comparison of the numbers of female Mediterranean fruit flies captured with two versions of the novel trap versus a standard water and protein-baited glass trap (bars), and the percentage of unmated flies per trap (pie slice) using a low dose of synthetic bait. Bars having the same letter are not significantly different.

DETAILED DESCRIPTION THE INVENTION

Figure 1A:
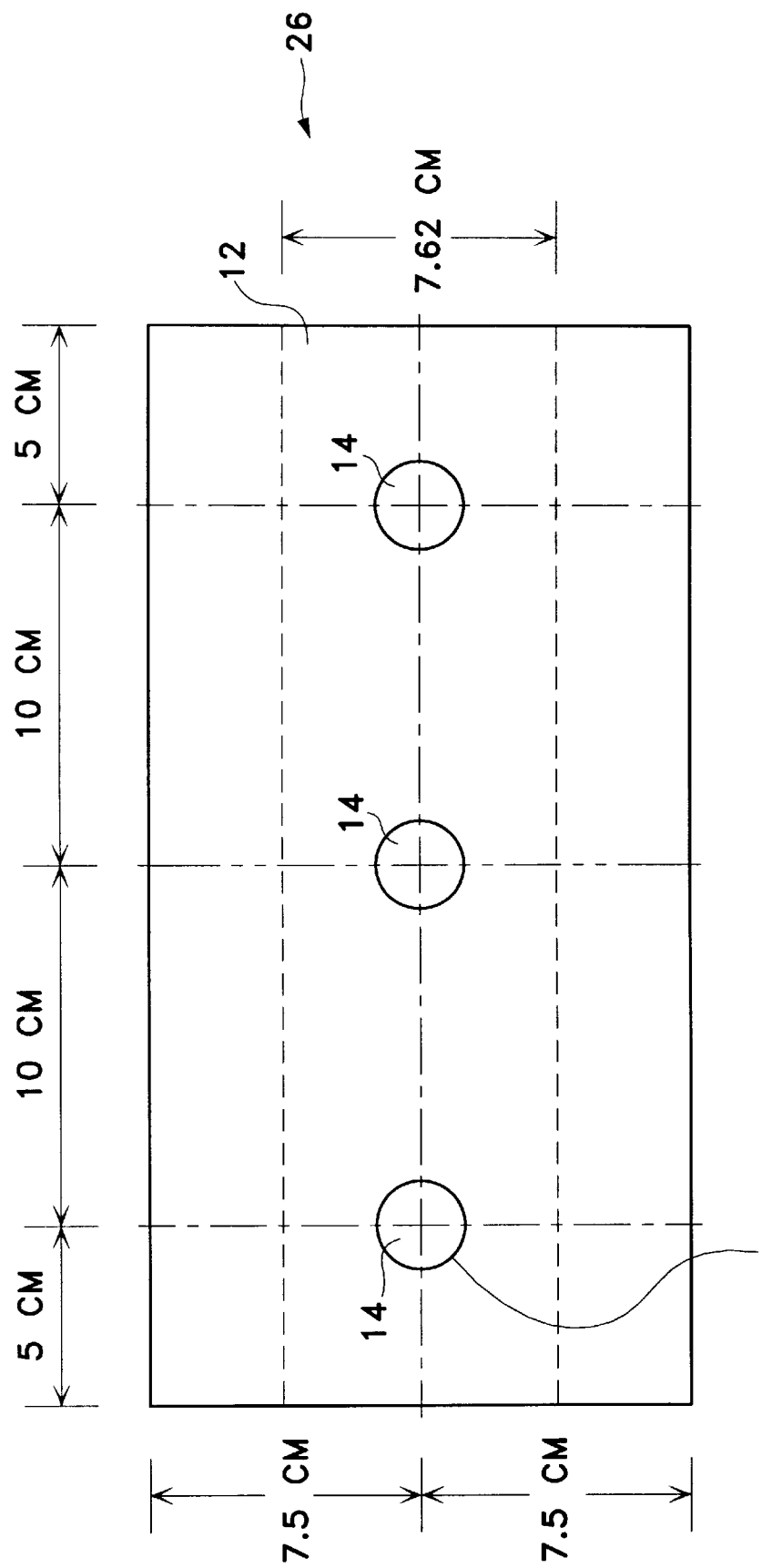
FIG. 1a shows the body of the trap in a single plane.

The invention provides, for the first time, a system for monitoring and/or controlling fruit flies without using aqueous protein solutions. The method and apparatus of the invention incorporate a unique combination of visual and chemical stimuli which not only attract fruit flies but induce them to enter a cylinder so that they can be trapped, killed or otherwise controlled. We have discovered that we can combine a visual stimulus, which mimics the host fruit or foliage, with two chemicals isolated from food baits—ammonia and 1,4 diaminobutane (putrescine). When these two chemicals are present in effective amounts, the apparatus not only attracts the flies but also causes them to enter the trap, retains the flies in the trap, and kills the trapped flies by inducing them to feed on a panel inside the trap that contains a visual cue, a feeding stimulant and a toxicant. This is also the first use of a combination of an external visual cue, synthetic food-based chemicals, and a feeding stimulant with toxicant that causes death of fruit flies responding to the apparatus. The attraction and capture of fruit flies with a cylindrical trap baited with a synthetic chemical blend was unexpected because prior art teaches that fruit flies do not respond to cylindrical shaped visual cues (Nakagawa et al., Entomol. Exp. Appl., 1978 supra).

Additionally, it was discovered that female fruit flies of different physiological ages can be selectively attracted by a well defined release of attractive chemicals. The ability to attract females before they mate adds greatly to the value of the trapping system because it permits the elimination of females before they oviposit in fruit.

Although it is known that numerous chemicals are released from protein baits the attractiveness of some of these chemicals released at various doses was heretofore unknown. Specifically, although ammonia has been suggested as an attractive chemical for many fruit flies, only moderate attractiveness to, for example, the Mediterranean fruit has been observed (Baker et al., Journal of Economic Entomology 83: 2235–2245, 1990). Although a commercial formulation containing ammonium acetate is available that will release ammonia, no reliable quantitative data is available regarding the release rate of ammonia from this formulation. Furthermore, methods to vary the release rate of this formulation heretofore were undescribed. We have discovered that a blend of ammonia (from an ammonium acetate formulation) and putrescine is needed for attraction of fruit flies. We have discovered that female fruit flies, depending on their physiological state, prefer different release rates of this blend. Based on this discovery, for example, traps may be designed to capture sexually-immature unmated, sexually-mature unmated or sexually-mature mated female fruit flies by varying the amount of the chemical blend released.

The unique aspects of the trap design include both conceptual and analytical aspects of fruit fly behavior. The design of the cylindrical trap is unique and provides a three dimensional shape that, when viewed by the fly, apparently mimics a fruit host. Similarly because fruit flies fly upwind to attractive odor sources a trap with at least three holes offers a system in which chemicals are released independent of wind direction. Additionally, the emission of chemicals from inside the trap entices the flies to enter the trap. The design of the trap permits a multitude of color combinations to be used. The trap design was particularly difficult to make because nothing in the prior art provides the necessary mechanisms the would result in retention of the trapped flies without the use of sticky materials. Based on observations of the behavior of flies that have entered the trap, we have discovered that a translucent nature of the painted trap results in the inability of the trapped flies to discern that the hole from which they entered could also serve as an escape hole. Flies inside the traps typically walk around the perimeter of the hole and avoid the bright light of the hole itself. The trap design has translucent, clear, or light passing zones at the top and bottom and, in addition to serving as a structural support for the cylindrical shape, the clear areas at the top and bottom take advantage of the instinctive response of flies to be positively phototactic (move toward light). This response facilitates the movement of the captured flies towards the top or bottom of the trap in what is perceived as an escape mechanism but instead, results in flies alighting on colored panels that also may be partially or wholly translucent containing a strong feeding stimulant combined with a toxicant. Prior art teaches that fruit flies that touch sugar, such as sucrose, with their tarsus (feet) begin a rapid feeding response to the sugar and that a toxicant can be mixed with the sugar and thus provide a lethal system to the flies. Previously documented systems employ granulated materials and do not provide instructions on how to combine a visual cue with a feeding stimulant and toxicant. Through a series of research efforts we have discovered that a formulation of an aqueous solution of sucrose and toxicant can be mixed with paints that are water-based. This unique formulation can be painted on a surface and, using the paint as a visual cue, this combination attracts flies inside the trap to the specific areas that contain the feeding stimulant and toxicant. The toxicant is contained within the trap, and a minimum concentration of toxicant is needed per trap due to the combination of feeding stimulant and visual cue presented with the toxicant. The placement of the toxicant system within the trap is critical to protect the toxicant from adverse environmental conditions which may cause deterioration of the toxicant system. Specifically, exposure to water (i.e. rain) would result in loss of feeding stimulant due to the solubility of sucrose in water.

The novel combination of visual and chemical stimuli of the invention provides a tool for fruit fly detection and population density estimation as well as a means for control of these pests. The ability of the invention to attract both sexes of the fruit flies suggests the following benificial economic applications: (1) the detection of a new infestation; (2) the monitoring of existing adult populations in order to predict future infestation levels to better schedule (and reduce) treatment with conventional pesticides; and (3) the control of reproduction in adult populations by attracting a demographically significant portion of the female population for subsequent destruction.

A particular advantage of the invention is that it includes chemicals that are food-based attractants and that it attracts both female and male fruit flies. Because the invention results in the trapping or death of the female fruit flies that are either sexually immature, sexually mature unmated or mated, it directly removes reproductive potential from the field, effectively reducing potential populations of the pest fruit flies and saving fruit and vegetables from infestation.

Another advantage of the invention is that it allows detection of populations and changes in populations of fruit flies, and provides a means to control these fruit flies in fruit crops to reduce or prevent losses caused by the pests.

There are several features of the invention which influence its functioning and efficiency. These include the color of the visual stimulus and the release rate of the chemical stimulus. The performance of the invention when placed in a host tree is dictated by the attractiveness of the chemicals that bring the flies to the vicinity of the trap and by the short range response of the flies to visual characteristics of the visual stimuli.

The Mediterranean fruit fly, *Ceratitis capitata,* is used as a model system. However, the system is applicable to the control of other frugivorous pest insects. One of ordinary skill in the art could readily determine which visual cues are needed to capture specific tephritid fruit fly population.

TRAP CONSTRUCTION

Figure 1B:
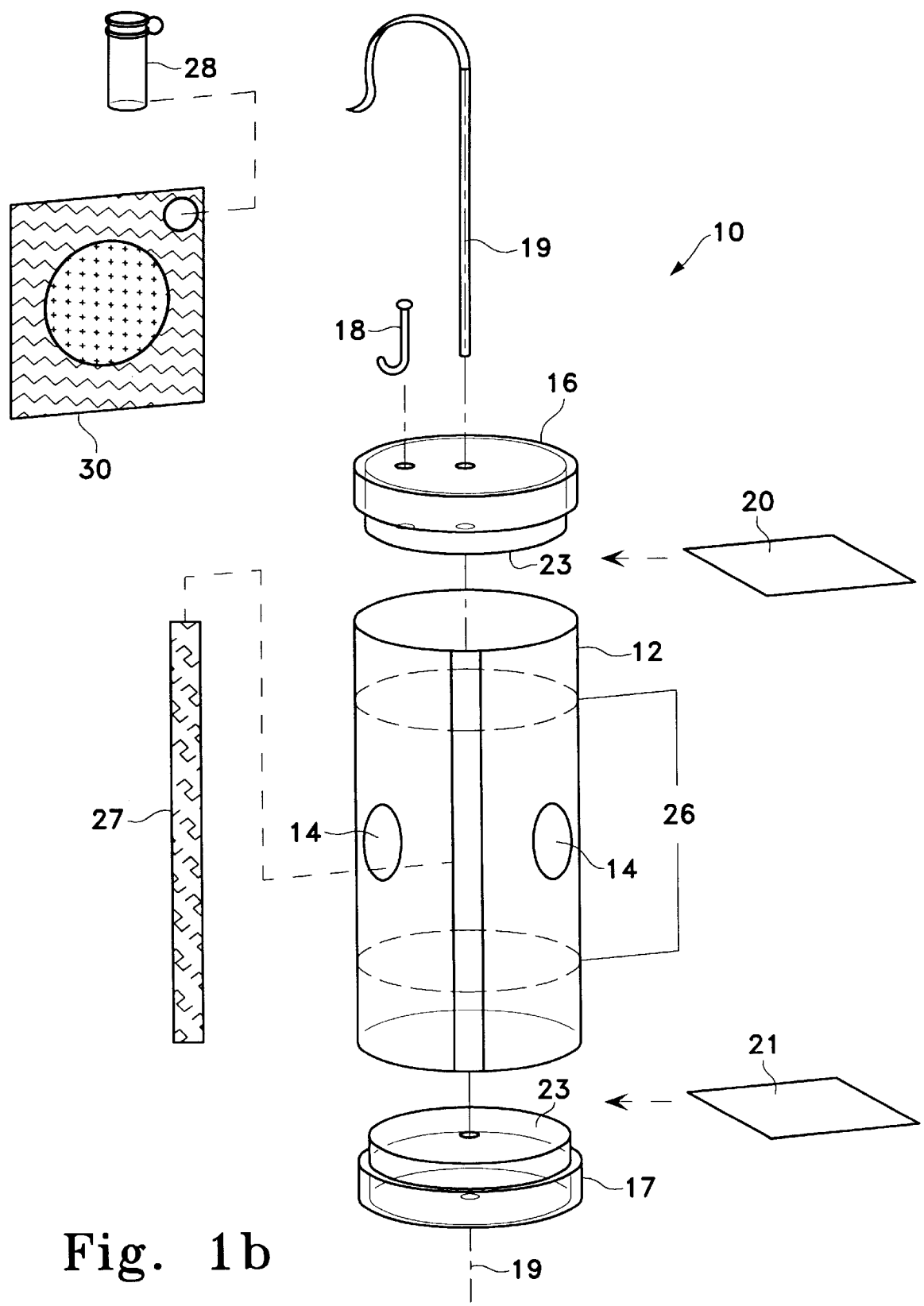
FIG. 1b shows the apparatus of the invention in exploded view.

The trap 10 (FIG. 1b) consists of three major components; the main trap body 12, which is at least a partially painted cylindrical container made from any suitable clear, flexible material such as LEXAN®, acetate sheeting, MYLAR®, butyrate, BIVAX®, and ACRYLITE®, for example, having at least three holes 14 (FIG. 1a) that allow insect entrance, and contains bait 28, 30 and toxicant 20, 21; two removable end caps 16, 17 for quick access into the trap for insect removal, trap cleaning, and bait replacement; two wire hangers 18, 19, which may be frictionally fitted to the ends of the trap body 12, one 18 for attaching baits 28, 30 inside trap 10 and another 19 for holding the trap together and supporting the complete assembly on a tree (FIG. 1b). Synthetic chemical bait 28, 30 to attract fruit flies and two toxicant panels 20, 21 to kill responding insects are placed inside the dry trap. The main body 12 is a 15.0 cm wide× 30.0 cm long rectangular piece of 0.025 mm thick clear flexible material cut, for example, from a 1.0 m wide×30.5 m roll of Grafix clear acetate sheeting (P/N# 44008, United States Plastics Corp., Lima, Ohio). Three 2.2 cm diam holes 14 are cut out along the lengthwise centerline spaced 10 cm apart left and right of center. A 7.62 cm wide strip 26 on the main body 12, also centered along the lengthwise axis of main body 14 (3.81 cm from each outside edge) is spray painted to provide a visual cue. In this investigation one of three glossy colors which can be used, for example is fluorescent green, yellow or orange (ColorWorks Fluorescent Spray paints, Krylon Division of the Sherwin-Williams Co., Solon, Ohio). The painted rectangular piece of plastic is rolled into a 9.0 cm diam cylinder, with the painted surface facing inside, and the overlapping ends taped together using a 15 cm long piece 27 of 1.27 cm wide Scotch™ Brand double-sided tape (3M Corp., St.Paul, Minn.). The exterior of the dry trap can be coated with a sticky material such as, for example, TANGLE TRAP® Adhesive and TANGLE-FOOT®.

Figure 1C:
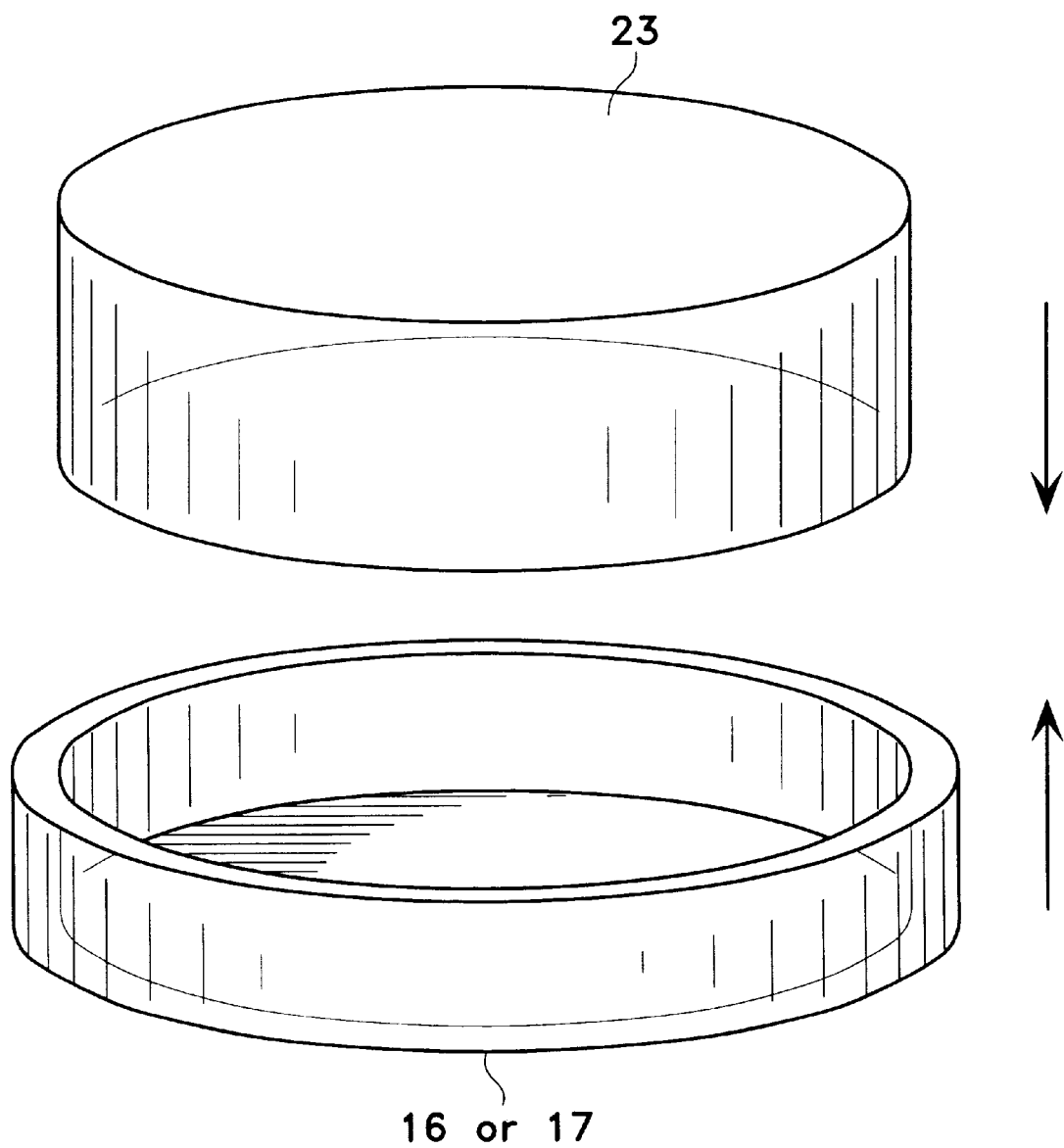
FIG. 1c shows the assembly of an end cap of the device of the invention.

The two removable end caps 16, 17, one for the top and one for the bottom, are made using, for example, standard 100×15 mm laboratory grade plastic petri dishes (P/N# 3488-B28, Thomas Scientific, Swedesboro, N.J.). The two halves (FIG. 1c) of the petri dishes are glued together using methylene chloride. Since one half is smaller and fits inside the other, the resulting union forms a small groove into which the wall of the plastic cylinder (main body) may be frictionally fitted.

Both the top and bottom end caps have a 0.16 cm hole drilled completely through the center. A 35 cm piece of 20 gauge galvanized steel wire 19 is threaded through the entire assembly and bent at a 90 degree angle after it exits the bottom end cap, thereby holding the dry trap together. The top section of the wire is bent into a hook for hanging onto a tree. In addition to the center hole on the top end cap, a second 0.16 cm hole is drilled 1.0 cm next to it to allow for another small piece (10 cm long) of the same steel wire 18 bent into a hook, to be used as a hanging point for chemical baits 28, 30 within the trap.

TOXICANT PANELS

Two small painted cardboard panels 20, 21 (FIG. 1b) containing a feeding stimulant and toxin are placed on surface 23 (FIG. 1b) of the end caps using double-sided tape, and are used for killing flies that enter the trap. The toxicant used is, for example, technical grade methomyl (E. I. DuPont De Nemours and Co., Newark, Del.; 98% [AI]). Other suitable toxicants, for example, are malathion, dichlorvos, and naled. ACS grade sucrose (Mallinkrodt, Paris, Ky.) is used, for example, as a feeding stimulant. Any sugar could be used. The color visual cue is, for example, Hunter Green 100% Acrylic latex paint (The Glidden Co., Cleveland, Ohio). The panel may be of a color different from the color applied to the cylinder. Additionally the panel may, for example, be a piece of colored cardboard to which a sugar/toxicant solution and/or a sticky material is applied.

A ratio of 1.0:0.5:0.01 of paint/sugar/pesticide is prepared by dissolving 18 mg of pesticide in 0.8 ml of water, and then adding this to a premixed sugar solution (1 g sucrose in 3.2 ml water). After the pesticide and sugar mixture is combined, 2.0 g of paint is added and the mixture stirred. A 13×8 cm rectangular piece of waxed cardboard is used as the substrate for the toxicant solution. A 5 mm wide×1 mm thick outside border is made using teflon adhesive tape (Batik Protective Overlay, Berghol America, Concord, Calif.) to maintain the solution on the cardboard. A total of 3.4 g of solution is transferred to a panel within 2 hr of preparation and allowed to air dry prior to use. The panel is cut into eight 4×3.25 cm pieces and two of these panels are placed on surfaces 23 of end caps 16 and 17 in each trap.

SYNTHETIC CHEMICALS AND RELEASE RATES USED FOR ATTRACTION

Our research shows that ammonia and putrescine are released by protein baits and that when ammonium acetate and putrescine are used in combination without interference from other chemicals released by protein baits, they are highly attractive to fruit flies. Ammonia, acetic acid (from ammonium acetate) and putrescine are used in combination with the visual stimulus in an effective amount. An effective amount is defined as that quantity of chemical blend that provides a release rate of the blend from a membrane that attracts fruit flies to the location of a bait at a rate significantly higher than flies are attracted to a nonbaited location. Ammonium acetate is contained in a release membrane made from, for example, polyethylene, polypropylene, polyvinylchloride, mylar, and acrylic as described in Leonhardt et al, Insect Pheromone Technology: Chemistry and Applications, ACS Symposium Series 190, 1982 and Kydonisus, Controlled Release Pesticides, ACS Symposium Series 53, 1977; which are herein incorporated by reference. A commerically available preparation of ammonium acetate from a release membrane called BioLure® (Consep Membranes Inc., Bend, Oreg.) can also be used. Additionally, the amount of ammonia and acetic acid can be quantified as described in Example 1 below. A preferred release rate range for ammonia is approximately about 40 ug/hour to 600 ug/hour. A more preferred range of release rate is 45–400 ug/hour. A most preferred amount is 45, 120, and 400 ug/hour for the low, medium, and high dose respectively. A preferred release rate range for acetic acid is approximately about 1.0 ug/hour to 16 ug/hour. A more preferred range of release is 1.5 to 13 ug/hour. A most preferred amount is 1.5, 3, and 13 ug/hour for low, medium, and high dose respectively. 1,4 diaminobutane is placed in a vial as a substantially pure liquid preparation. A preferred range for 1,4 diaminobutane is approximately about 25– 300 ul of a substantially pure liquid preparation (neat) of 1,4 diaminobutane. A more preferred range is approximately about 50–200 ul of a substantially pure liquid preparation 1,4 diaminobutane as described above. A most preferred amount is 50, 100, and 200 ul for a low, medium and high dose respectively. The release membrane 30 and vial 28 are each hung from wire hanger 18. However, the patch and vial can be placed anywhere inside of the main trap body. Factors such as insect population density, age-structure of the target population, temperature, wind velocity, and release rate will influence the response of the flies and thus the actual number of flies trapped. Factors such as temperature, wind velocity and release substrate will influence chemical release rate. The amount of compound in a particular set of circumstances that will provide a release rate within the effective range can readily be determined by a dose response field test as described in Example 2 below. Few males or females were caught in the blank or in the putrescine-only baited traps. Except for the male Mediterranean fruit flies in the medium dose trials, ammonium acetate alone was significantly better than either blank or traps baited with putrescine only. The addition of putrescine to the ammonium acetate, however, significantly increased percentage capture of females over ammonium acetate alone at either dose and significantly increased capture of male fruit flies over all other medium dose traps. The combination may be described as synergistic for Mediterranean fruit flies and possibly for other fruit flies.

COLOR OF THE TRAP

Trap color significantly affects capture of fruit flies. Significantly more female Mediterranean fruit flies are trapped in green traps than in clear traps. Male Mediterranean fruit flies preferred yellow traps, and capture in yellow traps is significantly greater than that in orange traps. Mexican fruit flies (*Anastrepha ludens* [Loew]) do not differentiate among any of the colors. However, the percentage of trapped Mexican fruit flies is significantly higher in colored traps than in clear traps. Details on experiments that were conducted to determine of effect of the color of the trap on the attraction of fruit flies are described in Example 2.

USES OF THE INVENTION

The invention is used as a monitoring, control, and/or detection tool. One method is to deploy the trap and tabulate the catch to determine size and location of fruit fly infestation. Economic use of appropriate pest management systems can then be determined. The method of trapping the flies can also serve as a control method and is described in detail below in Example 3.

The invention is used in combination with insecticide application or other control measures. The invention is used to attract flies and to induce them to enter a trap where they contact an effective amount of toxicant to achieve control. An effective amount of the toxicant is an amount that is lethal for an exposed insect or at least sublethal but sufficient to incapacitate the insect in regard to future mating or oviposition activity. Illustrative of the wide variety of toxicants which may be used with the invention are, for example, methomyl, malathion, dichlorvos and naled or a combination of two or more.

Another method is for control of fruit flies by using the invention to detect the location and boundaries of localized fruit fly infestations and employ in the area chemosterilants, bioregulator agents, parasites, predators or other biological control agents for fruit flies.

EXAMPLES

The following examples illustrate the use of the invention for the control of frugivorous pest insects using the Mediterranean fruit fly as a test model. They are intended to further illustrate the invention and are not intended to limit the scope of the invention as defined by the claims.

Example 1

The effective release rate of ammonia from the chemical bait was determined.

Chemical Lures

The synthetic bait used in this study is a blend of ammonia, acetic acid and 1,4 diaminobutane (putrescine). A commercial formulation containing 7 grams of ammonium acetate from a release membrane was used for all studies (BioLure@, Consep Membranes Inc., Bend, Oreg.). The formulation releases ammonia and acetic acid as volatiles. The release rate from the ammonium acetate patch was adjusted by changing the exposed area of the release membrane. The area of exposed surface of the membrane tested was 1.0 $cm^2$ (low dose), 1.4 $cm^2$ (medium dose) and a full patch having a membrane surface of 4.0 cm in diameter or a 6.3 $cm^2$ area (high dose). A substantially pure preparation of putrescine was tested neat in a small vial at 50, 100 or 200 ul per vial (low, medium and high dosages, respectively).

The release rates of ammonia from the patches with the three dosages were determined using an ammonia-specific ion-selective electrochemical probe (Orion, Boston, Mass.). A patch was placed in an Erlenmeyer flask, the flask purged for 1 h with an air flow of 1 liter per min, and volatiles were then directed to a sparge system that consisted of a gas dispersion tube (#7198 Ace Glass, Vineland, N.J.) placed in a graduated cylinder containing 100 ml of 0.05 N HCl solution. After a collection, the ionic strength of the sample solution was adjusted using 5M NaOH/0.05M disodium EDTA/10% methanol containing a color indicator. A standard ammonium calibration curve was prepared each day an analysis was done. The average release rates from low, medium and high dose patches were obtained after various periods of exposure during 39, 38 and 28 day periods, respectively. Patches were placed in a laboratory hood with a wind flow of approximately 0.22 m per sec at approximately 23° C. when not being analyzed.

Figure 2:
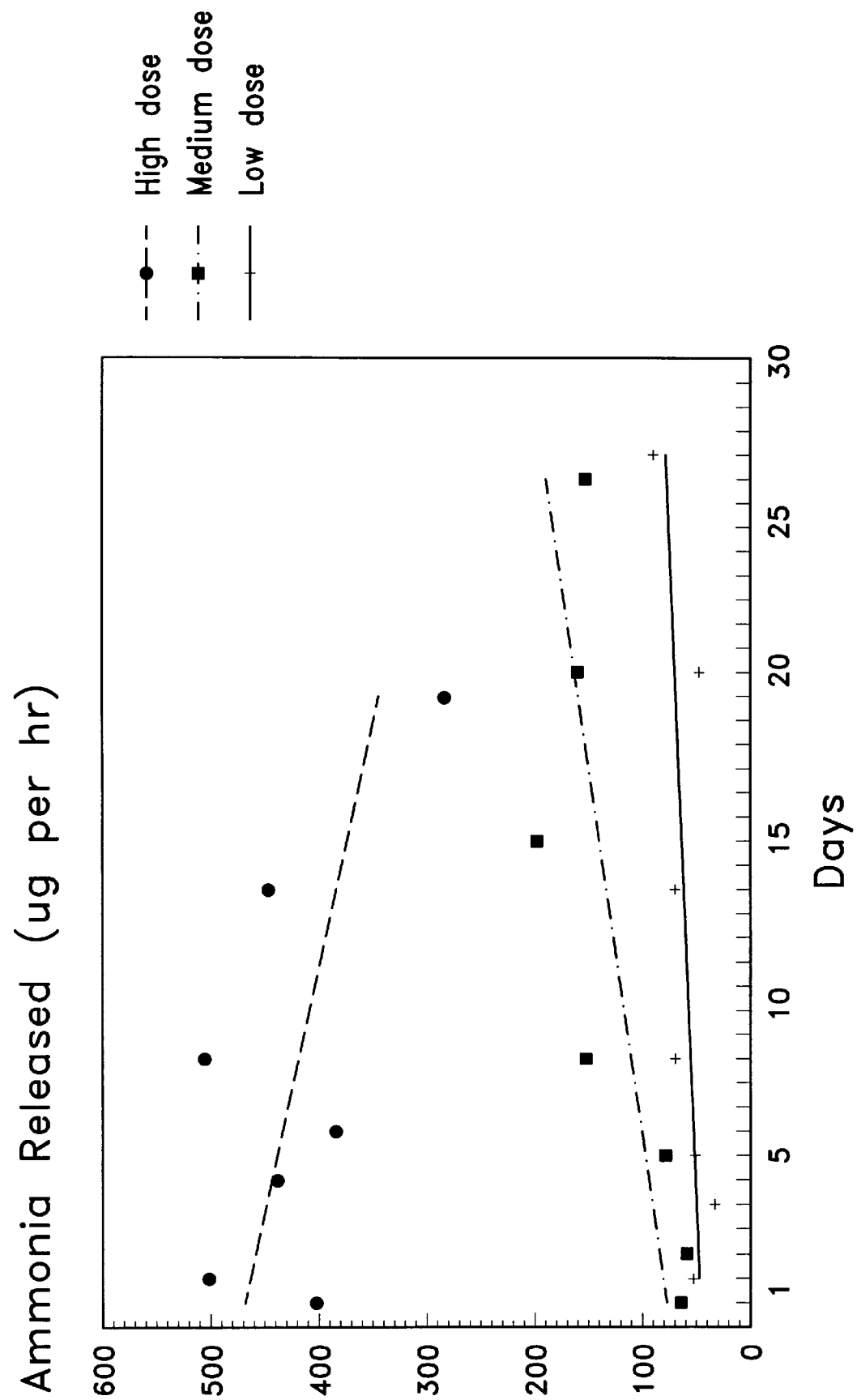
FIG. 2 shows the release rates of ammonia that were used in low, medium and high dosage experiments.

Results from release rate studies of the ammonium acetate patches are shown in FIG. 2. There was a significant increase in release rate of ammonia over time (days) for the medium dose only. Release rate decreased slightly, but not significantly, over time for the high dosage patch, and remained constant for the low dosage patch. The initial release rates [±SD] of ammonia from the low and high dose patches were 44.6±4.9 ug per h and 405.2±168.7 ug per h, respectively. The release of ammonia at the high dosage was relatively constant for the first 21 days that the patches were analyzed.

Currently there is are no analytical method available to quantify the release rate of putrescine. Due to the hygroscopic nature of putrescine the use of weight loss of material is compromised. Observation of decrease in amount of putrescine in a vial, over time, indicated that relative release rate was proportional to the amount of material in the vial. That is the original load of 50, 100 and 200 ul of material would provide relative release ratios of 1x:2x:4x respectively.

Example 2

Field tests to demonstrate the significance of the two component chemical and significance of the trap color were conducted in finca Peruccini located in Palin, Guatemala. Orange, *Citrus sinensis* (L.), was in fruit during these trials and is a host for *C. capitata* and *A. ludens*. Traps were placed in orange trees for all trials, with standard protocol followed for trap placement within a tree (Anonymous, Florida Fruit Fly Detection Manual, USDA, APHIS, PPQ & FLDACS, DPI, Gainesville, Fla., 1989, incorporated herein by reference). Flies were removed from traps every 2–3 d, and numbers of male and female *C. capitata* and *A. ludens* were recorded. Initially, treatments were placed randomly within a tree, then traps were moved sequentially to the next position within the tree. In all tests, three sets of traps were placed in trees spaced approximately 20–30 m apart, and the total number trapped per treatment was determined from the sum of each sex and species collected that day. Thus, one replicate consisted of the sum total catch from three traps. Sum total was converted to percentage trapped per bait or trap type for analysis to facilitate comparisons among the range of fruit fly population sizes sampled. All experiments were replicated over time.

Choice tests were conducted to determine if both chemical components were needed for attraction of fruit flies (experiment 1) and to determine color choice (experiment 2). In experiment 1, traps were baited with ammonium acetate and putrescine, ammonium acetate alone, putrescine alone or left unbaited (control). Separate experiments were conducted for baits at the low and the medium dose and all trials were conducted using orange traps. There were 8 and 10 replicates of the low and medium dose trials, respectively. In experiment 2, the effect of trap color on fly capture was tested using traps that were clear, orange, green and yellow. All traps were baited with the medium dose of ammonium acetate and putrescine, and there were 19 replicates. The percentages of female and male *C. capitata* and *A. ludens* were analyzed with one-way analysis of variance using Proc GLM (SAS Institute, SAS/STAT Guide for Personal Computers, ver. 6 ed., SAS Institute, Cary, N.C., 1985) followed by LSD mean separation tests (P=0.05). Data was assessed by the Box-Cox procedure and transformed as necessary to stabilize the variance prior to analysis (Box et al., Statistics for Experimenters: An Introduction to Design, Data Analysis, and Model Building, J. Wiley & Sons, NY, 1978).

Figure 3A:
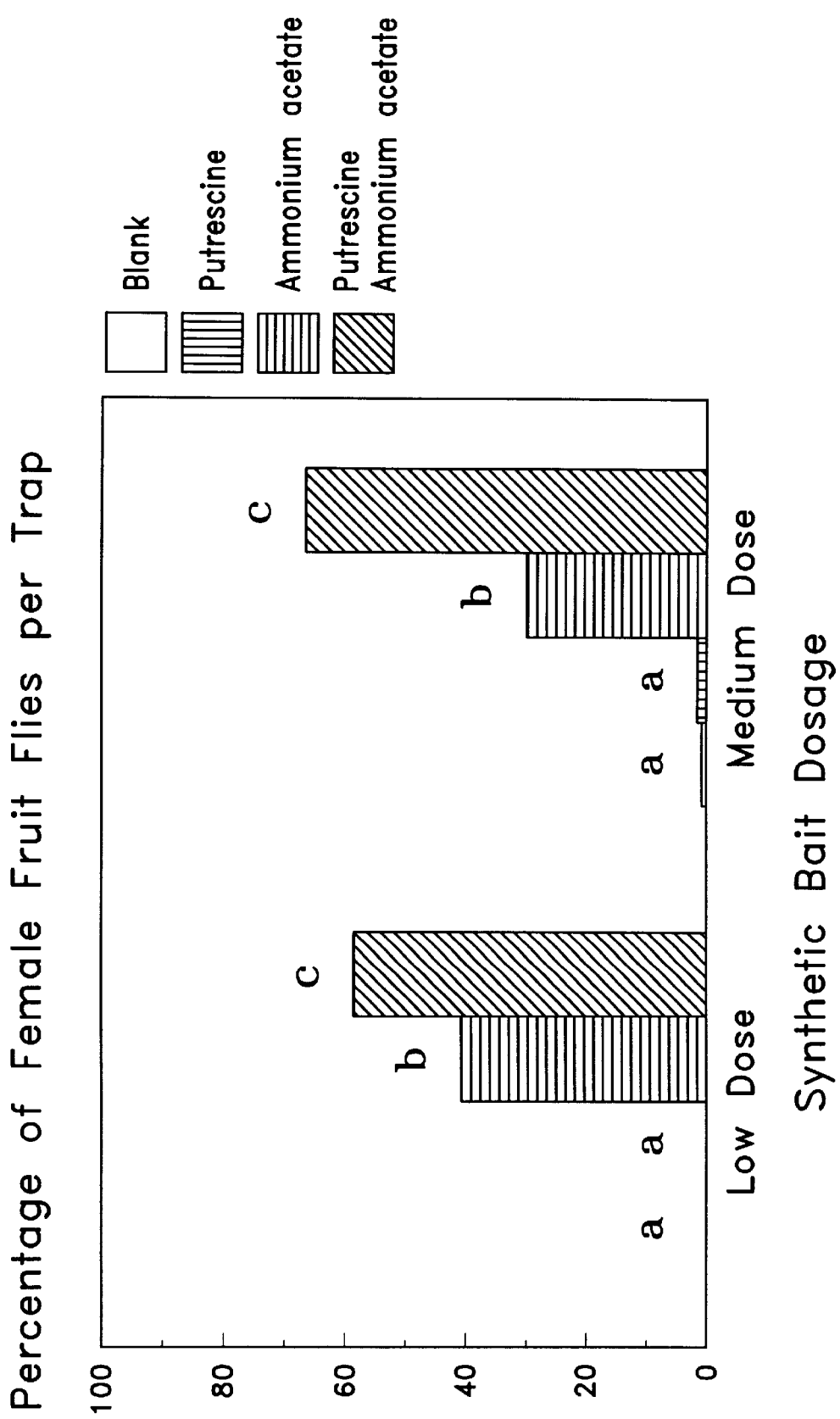
FIG. 3a shows the comparison of the percentages of female Mediterranean fruit flies captured with traps containing no chemicals, ammonium acetate only, putrescine only, and ammonium acetate and putrescine. Bars within a group (low dose versus medium dose) having the same letter are not significantly different.
Figure 3B:
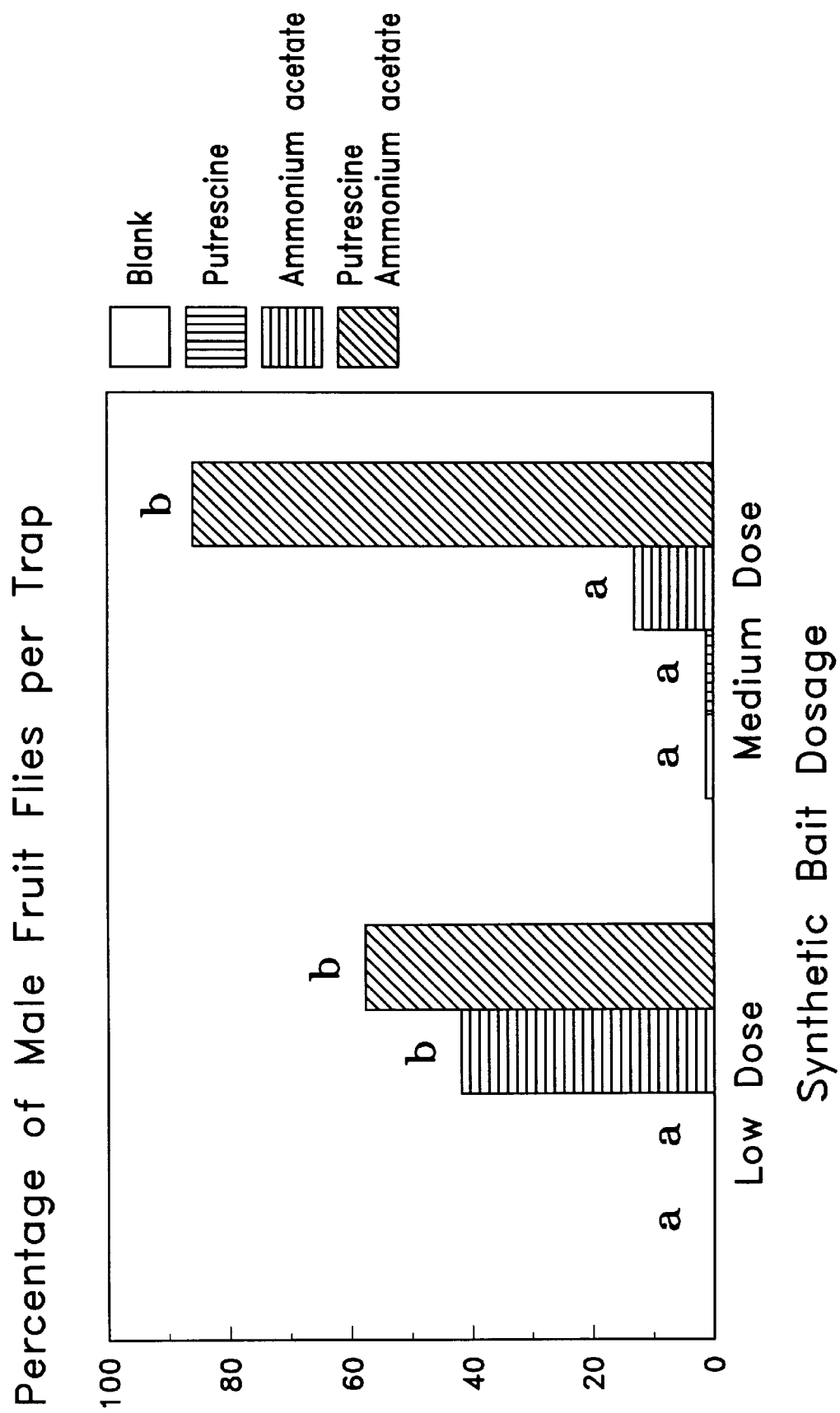
FIG. 3b shows the comparison of the percentages of male Mediterranean fruit flies captured with traps containing no chemicals, ammonium acetate only, putrescine only, and ammonium acetate and putrescine. Bars within a group (low dose versus medium dose) having the same letter are not significantly different.
Figure 4A:
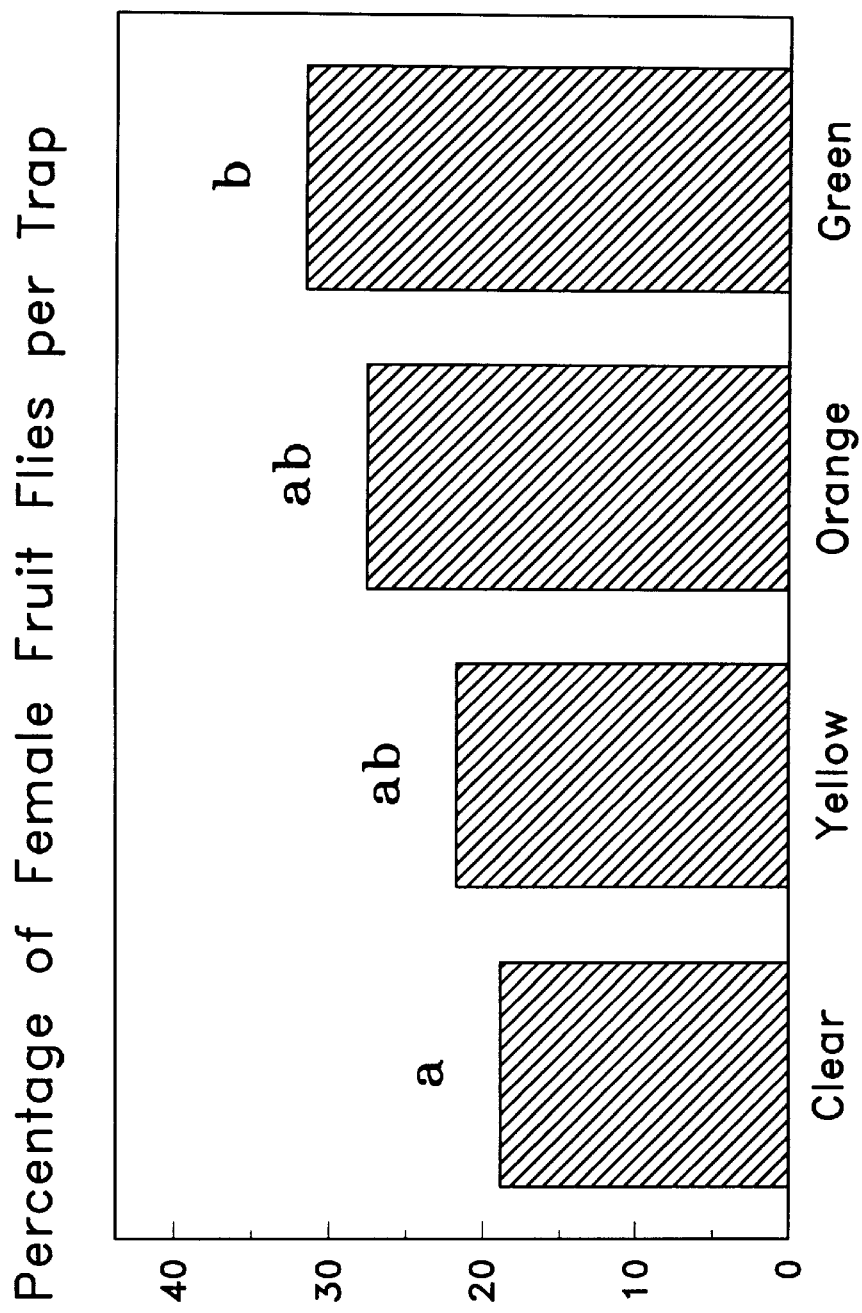
FIG. 4a shows the comparison of the percentages of female Mediterranean fruit flies captured using synthetic material with clear and different colored traps. Bars having the same letter are not significantly different.
Figure 4B:
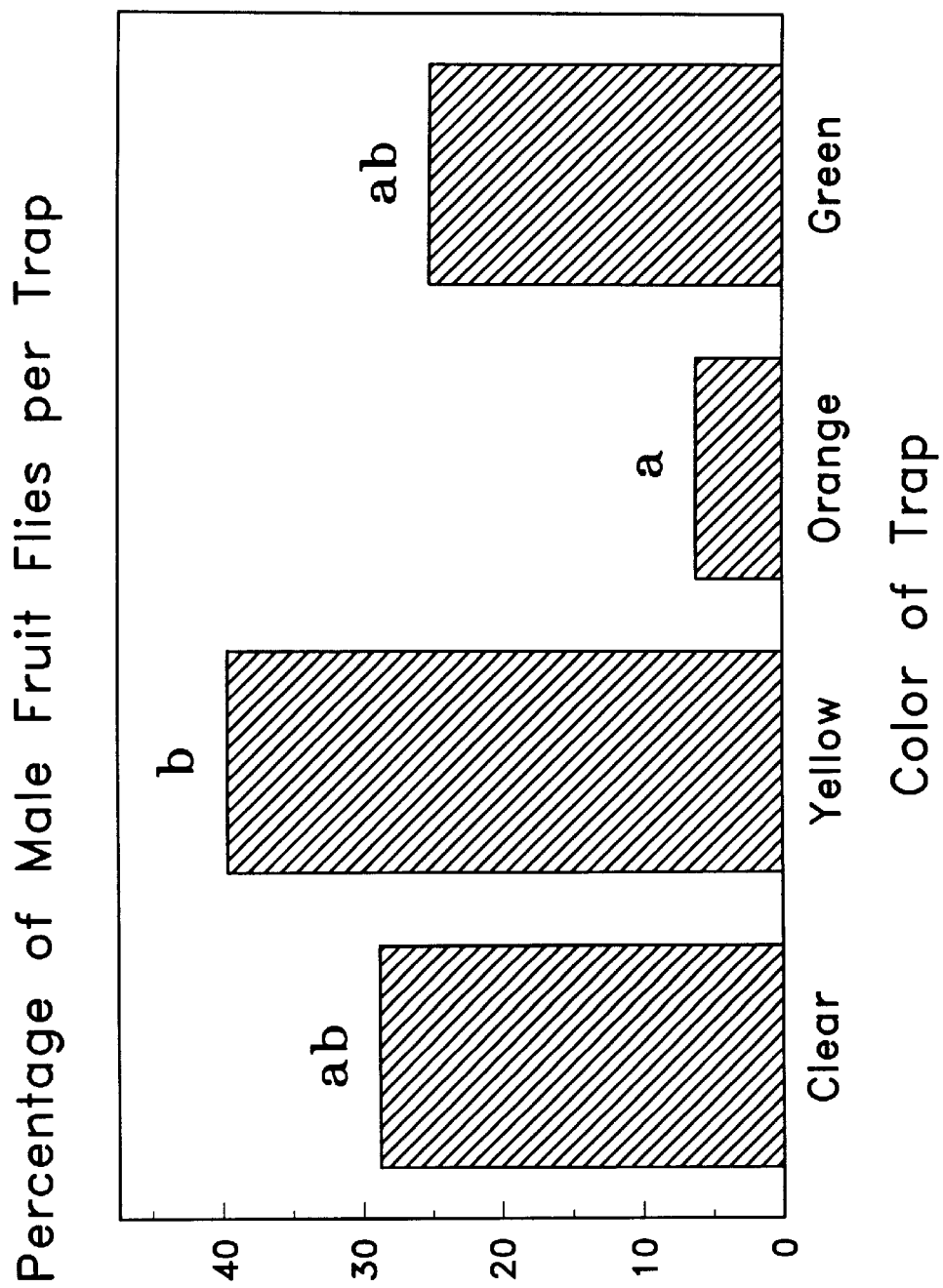
FIG. 4b shows the comparison of the percentages of male Mediterranean fruit flies captured using synthetic material with clear and different colored traps. Bars having the same letter are not significantly different.

Results of Experiment 1 demonstrated that few males or females of either species were caught in the blank or in the putrescine only-baited traps (FIG. 3 and Table 1 below). For all except the male Mediterranean fruit flies in the medium dose trials, ammonium acetate alone was significantly better than either blank or putrescine only-baited traps. Addition of putrescine to the ammonium acetate, however, significantly increased the percentage of captured females of both species over ammonium acetate alone at either dose, percentage capture of male Mexican fruit flies over ammonium acetate alone at the low dose, and percentage capture of male Mediterranean fruit flies over all other low dose traps at the medium dose. Tests conducted to determine the effect of trap color indicated that color significantly affected capture of fruit flies (FIG. 4 and Table 2 below). Significantly more female Mediterranean fruit flies were trapped in green traps than in clear traps. Male Mediterranean fruit flies preferred yellow traps, and capture of males in yellow traps was significantly greater than that in orange traps. Female and male Mexican fruit flies did not differentiate among any of the painted traps and percentage trapped in all colored traps was significantly higher than in clear traps.

TABLE 1

Comparison of the average percentages (SEM) of fruit flies captured in orange plastic insect trap containing synthetic baits at two doses in field trials conducted in Palin, Guatemala

|  | Blank | Putrescine | Ammonium acetate | Ammonium acetate + putrescine | F | P |
|---|---|---|---|---|---|---|
| Low Dose (n = 8) |  |  |  |  |  |  |
| *C. capitata* females | 0.0a (0.00) | 0.0a (0.00) | 41.1b (4.95) | 58.9c (4.95) | 213.1 | 0.0001 |
| *C. capitata* males | 0.0a (0.00) | 0.0a (0.00) | 41.9b (11.34) | 58.1b (11.35) | 18.7 | 0.0001 |
| *A. ludens* females | 0.8a (0.84) | 1.1a (1.07) | 42.9b (2.77) | 55.3c (3.19) | 208.8 | 0.0001 |
| *A. ludens* males | 0.0a (0.00) | 1.8a (1.79) | 33.1b (8.68) | 65.2c (9.53) | 29.7 | 0.0001 |
| Medium Dose (n = 10) |  |  |  |  |  |  |
| *C. capitata* females | 1.1a (1.11) | 1.4a (1.43) | 30.6b (5.25) | 66.9c (1.11) | 76.1 | 0.0001 |
| *C. capitata* males | 0.0a (0.00) | 0.0a (0.00) | 13.3a (13.34) | 86.7b (13.34) | 22.2 | 0.0001 |
| *A. ludens* females | 0.0a (0.00) | 2.0a (0.88) | 42.3b (4.96) | 55.8c (5.25) | 126.9 | 0.0001 |
| *A. ludens* males | 0.7a (0.71) | 0.0a (0.00) | 46.7b (4.34) | 52.6b (4.46) | 208.9 | 0.0001 |

Means within a row followed by the same letter are not significantly different (LSD mean separation test on square-root [x + 0.5] transformed data, P = 0.05).

TABLE 2

Comparison of average percentage (SEM) of flies captured in plastic insect traps painted different colors and in a clear trap baited with a synthetic bait in field trials conducted in Palin, Guatemala (n = 19)

| | Color of trap exterior | | | | | |
|---|---|---|---|---|---|---|
|  | Clear | Yellow | Green | Orange | F | P |
| *C. capitata* females | 19.2a (2.89) | 21.8ab (2.75) | 31.4b (4.55) | 27.6ab (2.84) | 2.52 | 0.0669 |
| *C. capitata* males | 28.9ab (11.15) | 39.7b (8.04) | 25.2ab (11.19) | 6.2a (3.24) | 2.55 | 0.0731 |
| *A. ludens* females | 15.4a (2.15) | 25.0b (2.49) | 27.2b (2.84) | 32.4b (2.90) | 8.26 | 0.0001 |
| *A. ludens* males | 12.7a (3.28) | 32.0b (4.45) | 28.6b (3.76) | 26.8b (3.52) | 6.76 | 0.0005 |

Means within a row followed by the same letter are not significantly different (LSD mean separation test on square-root [x + 0.5] transformed data, P = 0.05).

Example 3

The trapping efficacy of the green and orange plastic traps containing either low, medium or high dose of ammonium acetate and putrescine were compared with a McPhail trap baited with five torula yeast-borax pellets (ERA Int., Freeport, N.Y.). In no-choice tests, conducted at the same site used in Example 2, treatments were placed randomly in trees spaced approximately 20–30 m apart. Flies were removed from traps every 2–3 d, and numbers of male and female *C. capitata* and *A. ludens* were recorded. Traps were moved sequentially to the next position between trees when they were checked. Pellets were dissolved in 300 ml of water and placed in McPhail traps according to described procedures (Gilbert et al., Insect Trapping Guide, Pest Detection/Emergency Projects, State of California Department of Food and Agriculture, Sacramento, Calif., 1984). Water was added to the McPhail trap as needed during the two week period to maintain a volume of approximately 300 ml. New baits were made after two weeks of use. There were 18 replicates for each dose tested. The mated status of Mediterranean fruit fly females from the different traps was determined by dissecting a subsample of the trapped females, and checking for presence or absence of sperm in the spermathecae. Subsamples, consisting of ten flies dissected per trap type, were obtained from 5 replicates of each bait dosage. The numbers of female and male *C. capitata* and *A. ludens* captured were analyzed with one-way analysis of variance followed by LSD mean separation tests (P=0.05). Data was assessed by the Box-Cox procedure and transformed as necessary to stabilize the variance prior to analysis (Box et al., supra). Chi square analysis using Proc FREQ (SAS Institute, supra) of contingency tables of mated status by trap type within each dosage were used to compare mated status of females trapped.

Figure 5B:
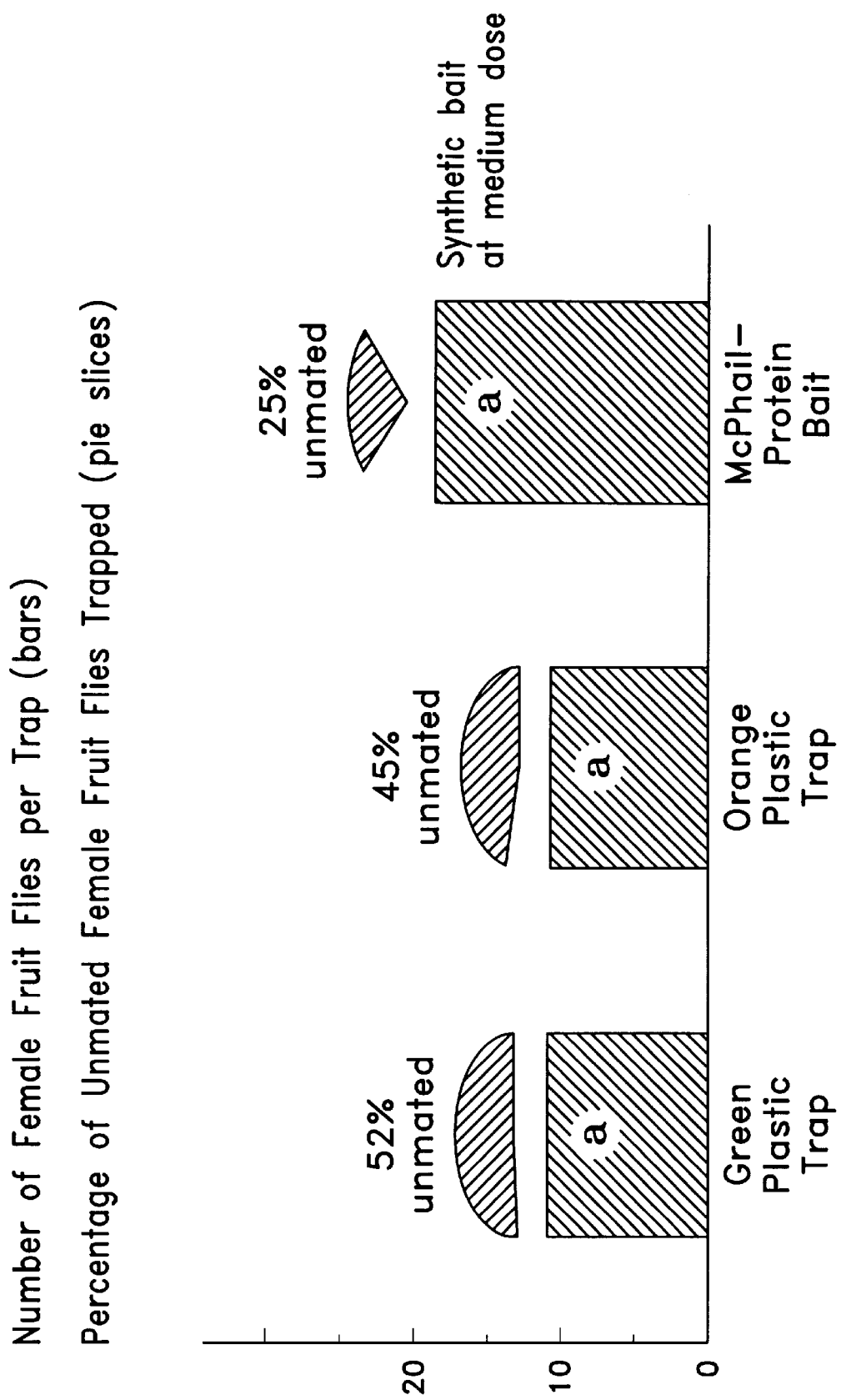
FIG. 5b shows the comparison of the numbers of female Mediterranean fruit flies captured with two versions of the novel trap versus a standard water and protein-baited glass trap (bars), and the percentage of unmated flies per trap (pie slice) using a medium dose of synthetic bait. Bars having the same letter are not significantly different.
Figure 5C:
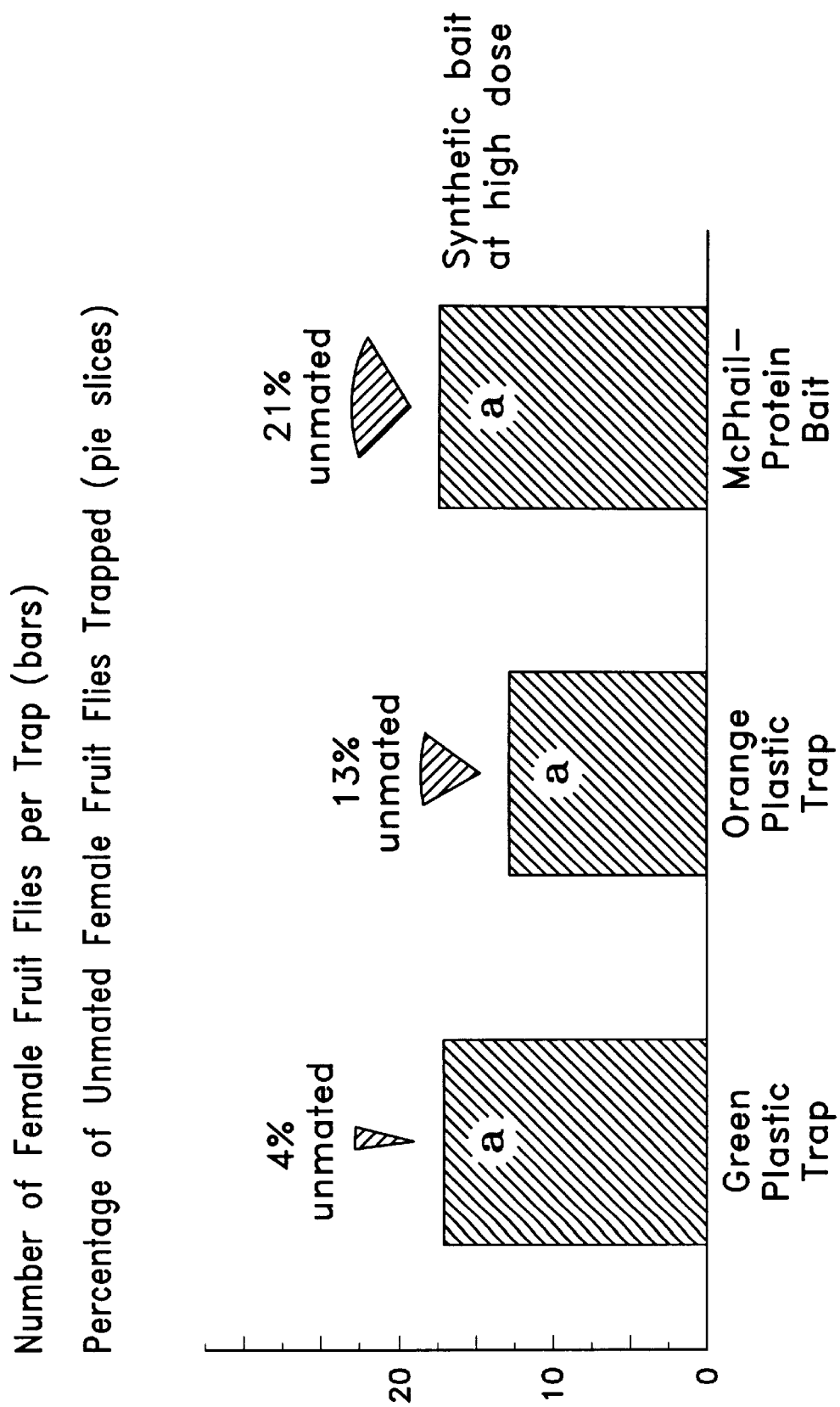
FIG. 5c shows the comparison of the numbers of female Mediterranean fruit flies captured with two versions of the novel trap versus a standard water and protein-baited glass trap (bars), and the percentage of unmated flies per trap (pie slice) using a high dose of synthetic bait. Bars having the same letter are not significantly different.

Comparisons of capture in orange and green traps baited with low, medium or high dosages of the synthetic blend with capture in McPhail traps are shown in FIG. 5 and Table 3 below. At the low dosage, the average number of flies captured in McPhail traps was significantly higher than in either plastic trap for both sexes of each fruit fly species, with the exception of the capture of male Mediterranean fruit flies. Green traps baited with the low dose of synthetic blend, however, caught a higher average number of male Mediterranean fruit flies than the orange traps with the same bait, and capture of males was not significantly different than in McPhail traps. There were no statistically significant differences among average number of male and female Mediterranean fruit flies captured by green or orange plastic traps baited with either the medium dosage or high dosage of synthetic blend or McPhail traps. Significantly more male and female Mexican fruit flies were caught in McPhail traps than in the traps of the invention at any of the tested dosages.

The comparison of the percentages of mated and virgin female Mediterranean fruit flies captured is shown in FIG. 5. At the low dosage of synthetic blend, percentages of unmated female Mediterranean fruit flies captured with the plastic traps (orange and green) were significantly higher than the percentage captured with McPhail traps. Percentage of unmated females captured was highest in green traps baited with the low dose of synthetic blend. Percentage of unmated females decreased at the medium dosage, although it was still significantly higher than the percentage among females from McPhail traps. The percentage of unmated female Mediterranean fruit flies captured was the lowest in the green traps baited with the high dosage of synthetic blend, and was significantly lower than percent unmated captured in McPhail traps. Trap capture of unmated females with orange traps baited with a high dose of synthetics was not significantly different than that observed with either the green trap or the McPhail trap.

TABLE 4

Comparison of the mated status of female Mediterranean fruit flies captured in plastic insect traps containing synthetic baits at three doses with standard McPhail traps baited with five torula yeast-borax pellets in field trials conducted in Palin, Guatemala (n = 50)

| Dosage of Synthetic blend | Unmated females trapped (%) | | | $Chi^2$ | P |
|---|---|---|---|---|---|
| | Orange | Green | McPhail | | |
| Low | 54.8b | 69.0b | 22.0a | 21.00 | 0.0001 |
| Medium | 45.4b | 51.7b | 25.0a | 7.25 | 0.027 |
| High | 12.6ab | 4.0a | 21.0b | 6.59 | 0.037 |

Chisquare analysis based on 2 by 3 contingency table within each dosage. Means within a row followed by the same letter are not significantly different (2 by 2 contingency tables of two-at-a-time comparisons within a dose, P = 0.05).

A comparison was made of target verses non-target flies captured with the plastic and McPhail traps. Of the total flies captured among the three synthetic dosages tested, non-target flies made up 2.1–5.5%, 3.7–7.0% and 39.3–60.2% of the catch in orange plastic, green plastic and McPhail traps, respectively.

The forgoing description is for the purpose of illustration. Others skilled in the art can apply the knowledge described

TABLE 3

Comparison of the average number (SEM) of fruit flies captured in plastic insect traps containing synthetic baits at three doses with standard McPhail traps in field trials conducted in Palin, Guatemala (n = 18)

| | Orange | Green | McPhail | F | P |
|---|---|---|---|---|---|
| Low Dose | | | | | |
| *C. capitata* females | 13.2a (2.08) | 23.6a (3.95) | 35.4b (5.46) | 8.0 | 0.0009 |
| *C. capitata* males | 4.8a (0.71) | 9.8ab (1.44) | 14.2b (2.37) | 13.0 | 0.0001 |
| *A. ludens* females | 6.8a (0.72) | 9.6a (2.03) | 83.4b (10.3) | 96.51 | 0.0001 |
| *A. ludens* males | 4.2a (0.51) | 5.4a (1.2) | 57.3b (8.60) | 80.2 | 0.0001 |
| Medium Dose | | | | | |
| *C. capitata* females | 10.6a (1.19) | 10.9a (2.11) | 18.6a (3.89) | 1.5 | 0.2342 |
| *C. capitata* males | 3.8a (0.62) | 3.4a (0.59) | 6.6a (1.65) | 0.6 | 0.5718 |
| *A. ludens* females | 7.3a (1.25) | 6.6a (1.28) | 59.1b (9.91) | 68.3 | 0.0001 |
| *A. ludens* males | 3.1a (0.59) | 2.2a (0.50) | 41.8b (0.59) | 74.2 | 0.0001 |
| High Dose | | | | | |
| *C. capitata* females | 12.6a (2.07) | 16.9a (4.44) | 17.2a (3.15) | 0.6 | 0.5535 |
| *C. capitata* males | 4.3a (1.18) | 6.2a (2.19) | 5.4a (1.32) | 0.1 | 0.8701 |
| *A. ludens* females | 4.2a (0.95) | 3.9a (0.81) | 23.2b (4.23) | 31.6 | 0.0001 |
| *A. ludens* males | 1.5a (0.33) | 2.4a (0.60) | 13.7b (3.35) | 26.6 | 0.0001 |

Means within a row followed by the same letter are not significantly different (LSD mean separation test on log [x + 1.0] transformed data, P = 0.05).

to other frugivorous pest insects. Such detail is solely for that purpose and those skilled in the art can make variations therein without departing from the spirit and scope of the invention.

INDEX OF ELEMENTS

10. Plastic dry trap
12. Main trap body
14. Holes
16. End cap
17. End cap
18. Inside wire hanger
19. Wire hanger
20. Toxicant panel
21. Toxicant panel
23. Inside surface of end cap
26. Visual cue on main trap body
27. Double-sided tape
28. Vial containing 1,4 diaminobutane
30. Ammonium acetate membrane

We claim:

1. An attractant for frugivorous pest insects consisting essentially of
   (a) ammonium acetate,
   (b) putrescine, and
   (c) a release membrane
wherein said (a) and (b) provide ammonia and acetic acid and putrescine in effective amounts for attracting frugivorous pest insects.

2. A synthetic attractant consisting essentially of compounds that release a gaseous composition consisting essentially of frugivorous pest insect attracting effective amounts of ammonia, acetic acid and putrescine.

3. The synthetic attractant of claim 2 wherein ammonium acetate is the compound which generates ammonia and acetic acid.

* * * * *